United States Patent [19]

Bertocchio et al.

[11] Patent Number: 5,650,545
[45] Date of Patent: Jul. 22, 1997

[54] SYNTHESIS OF PERFLUOROALKYL IODIDES

[75] Inventors: René Bertocchio, Vourles Par Vernaison; Patrick Lambert, Caluire; Georges Lacote, Chauffailles, all of France

[73] Assignee: Elf Atochem S.A., France

[21] Appl. No.: 452,759

[22] Filed: May 30, 1995

Related U.S. Application Data

[63] Continuation of Ser. No. 231,098, Apr. 22, 1994, abandoned.

[30] Foreign Application Priority Data

Apr. 27, 1993 [FR] France .................................. 93 04939

[51] Int. Cl.$^6$ ...................................................... C07C 21/18
[52] U.S. Cl. .......................................................... 570/172
[58] Field of Search ................................................. 570/172

[56] References Cited

U.S. PATENT DOCUMENTS 3,404,189  10/1968  Blockl.

FOREIGN PATENT DOCUMENTS 1096687  12/1967  United Kingdom.

*Primary Examiner*—Alan Siegel

[57] ABSTRACT

The invention relates to a continuous process for the preparation of perfluoroalkyl iodides by thermal telomerization, in the gas phase, of tetrafluoroethylene with pentafluoroethyl iodide or heptafluoroisopropyl iodide in a tubular reactor.

To improve the selectivity for a telomer of the desired extent, the telomers of lesser extent are recycled to at least one point in the reactor, which is situated between one-twentieth and three-quarters the length of the tube.

39 Claims, No Drawings

SYNTHESIS OF PERFLUOROALKYL IODIDES

This is a continuation of application Ser. No. 08/231,098, filed on Apr. 22, 1994, now abandoned.

FIELD OF THE INVENTION

The present invention relates to the field of perhalogenated aliphatic hydrocarbons, and more particularly to the preparation of perfluoroalkyl iodides RfI, Rf denoting a perfluoroalkyl radical which is linear and contains from 6 to 12 carbon atoms, or is branched and contains from 7 to 13 carbon atoms.

BACKGROUND OF THE INVENTION

These compounds are used as synthesis intermediates for numerous applications relating, in general, to the field of fluorinated surfactant substances and, more particularly, bases for fire-extinguishing formulations, hydrophobic and oleophobic finishing agents for the treatment of textiles or paper, and more recently applications of a medical nature (contrast agents or oxygen transporters).

The linear perfluoroalkyl iodides are customarily obtained by telomerization of tetrafluoroethylene with pentafluoroethyl iodide $C_2F_5I$, which is in turn prepared by the action of iodine and iodine pentafluoride on tetrafluoroethylene in the presence of a catalyst. These two reactions may be coupled, as described in patent FR 1 385 682, but in the majority of cases $C_2F_5I$ is prepared first and is then used in the telomerization. Branched perfluoroalkyl iodides can be obtained from a secondary perfluoroalkyl iodide such as heptafluoroisopropyl iodide $CF_3CFICF_3$.

The telomerization reaction can be carried out in accordance with at least three methods, which differ essentially in the means of activation, which may be:

- either free-radical activation using various peroxide initiators, as in the processes which are the subject of patents FR 2 035 913, FR 2 325 665 and U.S. Pat. No. 3,226,449,
- or catalytic activation involving the use of a redox system, as in the processes according to patents FR 2 028 781 and FR 2 098 335,
- or, finally, thermal activation, as in the processes which are the subject of patents FR 1 415 198 and U.S. Pat. No. 3,404,189.

In all of these processes, a more or less wide distribution of the various chain lengths is obtained and, even in the catalytically initiated processes which are reputed to be more selective, it is difficult to achieve a relatively narrow distribution for a telomer of extent j, j ranging from 2 to 5 and denoting the number of molecules or groups of tetrafluoroethylene which are telomerized with pentafluorethyl iodide or heptafluoroisopropyl iodide.

It is well known that this telomerization has the particular characteristic of giving products which may in turn function as telogen and may thus contribute to chain lengthening, a function which is almost exclusively performed by propagation reactions in the majority of telomerizations. In all of the text which follows, any perfluoroalkyl iodide may be considered as either a telomer or a telogen of extent i, $C_2F_5I$ or $CF_3CFICF_3$ being by definition only the telogen of extent 0.

In a large number of applications it is possible to use all of the telomers, or all at least of the fractions of extent i to j, j being an integer which is greater than or equal to i+1. On the other hand, certain applications necessitate the use of products which have a well-defined perfluorinated chain length.

Starting from a telogen of extent i, it is relatively easy to obtain the telomer of extent i+1 with a good selectivity, by reducing the degree of conversion by any suitable means (temperature, contact time, molar ratio telogen: $C_2F_4$). For a telomer of extent j where j>i+1, the problem is more difficult, and optimization is almost impossible without recycling some or all of the telomers of extent i+1 to j−1, with the risk of increasing the proportion of telomers with an extent greater than j, i.e. the fraction of unwanted, heavy products.

Patent Application EP 0 433 988 describes a more elaborate means of improving the productivity and of orienting the reaction towards the formation of specific compounds which have, in particular, well-defined carbon chain lengths. To achieve this objective, a part of the liquid reaction mixture is withdrawn from the second half of a tubular reactor and is reinjected, via a second loop, into the first half of the tube, such that the reaction space between the two points thus defined represents from 20 to 90 % of the overall reaction volume. On leaving the reactor the reaction mixture is fractionated; the heavy products of value are withdrawn from the apparatus and the light products and unused reactants are returned to the head of the reactor, where they are brought together with the feed of fresh reactants. In fact, if the sum of the products recycled via the first and second loops is taken into account, such a process involves a very large volume of recyclate in relation to the productivity of the apparatus, the mass of recycled products being from 80 to 200 times greater than the effective production, according to the examples given. Moreover, this process does not reduce the production of heavy telomers, since the ratios $C_8F_{18}I:C_{10}F_{21}I$+telomers of greater extents are equal to 2.1 and 1.45 for overall recycling rates of 200 and 80 respectively. The introduction of a second recycling loop increases the productivity of the system by about 20 to 30% but generates too high a proportion of heavy products which are of little or no commercial value, and the gains in selectivity for $C_8F_{17}I$ can only be obtained at the expense of making the recycling circuits a disproportionate size.

DESCRIPTION OF THE INVENTION

The object of the present invention is to achieve the optimal production, starting from a telogen of extent I, of a telomer of extent j where j>i+1, without either increasing the production of heavier products or causing an excessive drop in productivity.

To this effect it has been found that, by operating in the gas phase under conditions of thermal telomerization, where the latter is carried out in a tubular reactor, the recycling of telomers of extent i+1 to j-1 into the zone of the reactor situated between one-twentieth and three-quarters of its length results in a simultaneous improvement in the productivity of and in the selectivity for telomer of extent j, as opposed to the case where all of the recyclate is reintroduced with the fresh reactants at the head of the tube.

The invention therefore relates to a continuous process for the preparation of perfluoroalkyl iodides RfI by thermal telomerization, in the gas phase in a tubular reactor, of tetrafluoroethylene with pentafluoroethyl iodide or heptafluoroisopropyl iodide (i=0) or with a lower telomer with an extent i ranging from 1 to 3, characterized in that the telomers of extent i+1 to j−1, j denoting the extent of the desired telomer, are recycled to at least one point of the reactor which is situated between one-twentieth and three-quarters the length of the tube, preferably between one-fifth and two-fifths, the distances being taken from the tube inlet.

This process is advantageously carried out in a tubular reactor made of stainless steel or of nickel, which may have any shape and with a ratio of length to internal diameter of between 50 and 5,000, which is heated homogeneously over its entire length by an appropriate device to a temperature of between 300 and 365° C. At various distances from its inlet end, the tube comprises a certain number of apertures which enable the recycling of telomers of extent i+1 to j−1.

All of the telomers of extent i+1 to j−1 can be recycled to the same point in the tubular reactor. It is also possible to carry out a graduated recycling, in which the telomers of extent i+1 to j−1 are recycled to different points of the reactor depending on their extent, the lightest telomers advantageously being injected into an upstream zone of the reactor, situated between one-twentieth and one-third of its length, and the heaviest telomers in a downstream zone, situated between one-fifth and half the length of the tube.

The starting reactants, namely the taxogen ($C_2F_4$) and the telogen of extent i, are introduced at the head of the reactor by any appropriate means, for example using a metering pump for the telogen and a gas flow-regulating device for the $C_2F_4$.

Instead of introducing all of the tetrafluoroethylene at the head of the reactor, it is possible to introduce some of it (from 25 to 70%, advantageously from 40 to 60%) at at least one point of the tube which is situated between two-fifths and three-quarters of the length of the tube. Indeed, it has been shown in U.S. Pat. No. 5,268,516, of which the content is incorporated here by reference, that a graduated feed of this kind enables a reduction in the proportion of heavy telomers.

The products exiting the telomerization reactor are introduced into a soak column in order to separate the unconverted $C_2F_4$ and starting telogen and return them to the head of the reactor. The telomers are then fractionated in a first column in order to isolate the telomers of extent i+1 to j−1 and to return them to the reactor at the most suitable point for the selective production of the telomer of extent j, and are then fractionated in a second column in order to separate the telomer of extent j from the heavier products.

In accordance with a specific embodiment of the process according to the invention, the reactor is fed with fresh and/or recycled reactants in a manner which is advantageously regulated such that, in steady-state operation, the quantities of telomer of extent i+1 entering and leaving the reactor are substantially identical.

The molar ratio of the fresh reactants ($C_2F_4$ and starting telogen) which are fed into the reactor depends on the extent j of the desired telomer and on the required selectivity. The molar ratio of fresh telogen: fresh $C_2F_4$ may range from 0.1 to 0.6 and is preferably between 0.2 and 0.5.

In order to attain steady-state operation for the telomers of intermediate extent k (i+1≦k≦j−1) and in order simultaneously to improve selectivity for and productivity of the telomer of extent j, the molar ratios Tk=telogen of extent k:telogen of extent i will expediently be between 0.2 and 2, preferably between 0.5 and 1.4. These ratios are advantageously taken to be substantially equal to one another, although this does not constitute a limitation of the process.

In practice, the system is initiated with a portion of telogen of extent i to j−1 in the proportions defined above and with a feed of fresh reactants (telogen of extent i and $C_2F_4$) as defined by the extent of the telomer j, selectivity and the required productivity.

The telomerization reaction can be carried out within a temperature range of from 300° to 360° C., but is advantageously carried out at a temperature of between approximately 325° and 355° C.

On the industrial scale, it is possible to operate at atmospheric pressure or at a superatmospheric pressure, provided that the reaction system remains in the gaseous state.

EXAMPLES

The following examples, which are given without implied limitation, illustrate the invention for the production of perfluorooctyl iodide $C_8F_{17}I$ (j=3) from perfluoroethyl iodide (i=0). The percentages given are by weight.

The $C_2F_5I$ used is 99.87% pure, the principal impurities being $C_4F_9I$ (0.06%) and $C_2F_4$ (0.055%).

The $C_4F_9I$ used is 98.6% pure, the principal impurities being $C_2F_5I$ (0.1%), $C_6F_{13}I$ (0.2%) and perfluoroalkanes RfRf, in particular $C_8F_{18}$ and $C_{10}F_{22}$ (0.3%).

The $C_6F_{13}I$ used is 99.55% pure, the principal impurities being $C_8F_{17}I$ (0.1%) and perfluoroalkanes RfRf (0.25%).

Input/output evaluations of the various components of the reaction mixture permit the calculation of:

the composition of the fresh reactants fed in ($C_2F_4$ and $C_2F_5I$), the composition of the telomers produced, the productivity of telomer of extent j, expressed as grammes/hour/liter of reactor volume, the selectivity, expressed in relation to the masses of telomer of extent j and of teleomers of greater extent than j.

EXAMPLE A (Comparative)

A reactor is used which consists of a nickel tube 20 m in length and 4.3 mm in internal diameter, which is wound helically around a heating mandrel which enables the temperature of the tube to be maintained at 350°±5° C. over its entire length.

Introduced at the head of the reactor, via three metering pumps, are 229.8 g/h of $C_2F_5I$, 121.8 g/h of $C_4F_9I$ and 125.34 g/h of $C_6F_{13}I$, respectively, as well as 19.46 g/h of gaseous $C_2F_4$ via a device for regulation by mass.

The reaction mixture leaving the reactor is condensed through a water condenser and separated into a gas phase and a liquid phase, the compositions of which are determined by gas chromatography.

The mass balances of input and output are collated in the following table.

| COMPONENT | INPUT (g/h/l) | OUTPUT (g/h/l) |
| --- | --- | --- |
| $C_2F_4$ | 67.55 | 26.2 |
| $C_2F_5I$ | 791.9 | 756.2 |
| $C_4F_9I$ | 414.8 | 420.5 |
| $C_6F_{13}I$ | 431.1 | 440.9 |
| $C_8F_{17}I$ | 0.45 | 53.45 |
| $C_{10}F_{21}I$ | — | 6.9 |
| $≧C_{12}F_{25}I$ | — | 0.8 |
| RfRf | 3.9 | 7.5 |

Under these experimental conditions, which correspond to the reactor being fed with 41.3 g/h/l of fresh $C_2F_4$ and 35.7 g/h/l of fresh $C_2F_5I$, the production of telomers has the following distribution:

| | |
|---|---|
| $C_4F_9I$ | 7.5% |
| $C_6F_{13}I$ | 12.9% |
| $C_8F_{17}I$ | 69.6% |
| $C_{10}F_{21}I$ | 9.0% |
| $\geq C_{12}F_{25}I$ | 1.0% |

The selectivity is 6.96 for a productivity of $C_8F_{17}I$ of 53 g/hour per liter of reactor volume.

EXAMPLE B (Comparative)

A reactor is used which consists of a stainless steel tube 20 m in length and 4 mm in internal diameter, which is wound helically around a heating mandrel which enables the temperature of the tube to be maintained at 350°±5° C. over its entire length.

Introduced at the head of the reactor, via the same devices as previously, are 39.2 g/h of $C_2F_4$, 97.8 g/h of $C_2F_5I$, 27.6 g/h of $C_4F_9I$ and 41.4 g/h of $C_6F_{13}I$. Under these conditions, the composition of the reaction mixture leaving the tube at 344° C. is such that the mass of $C_4F_9I$ collected is equal to the mass of $C_4F_9I$ introduced.

The mass balances of input and output are collated in the following table:

| COMPONENT | INPUT (g/h/l) | OUTPUT (g/h/l) |
|---|---|---|
| $C_2F_4$ | 157.1 | 65.2 |
| $C_2F_5I$ | 391.1 | 324.7 |
| $C_4F_9I$ | 108.4 | 108.9 |
| $C_6F_{13}I$ | 163.8 | 188.3 |
| $C_8F_{17}I$ | 0.1 | 72.5 |
| $C_{10}F_{21}I$ | 0 | 35.5 |
| $\geq C_{12}F_{25}I$ | 0 | 25.2 |
| RfRf | 1 | 1.2 |

These operating conditions correspond to the reactor being fed with 91.9 g/h/l of fresh $C_2F_4$ and 66.4 g/h/l of fresh $C_2F_5I$. The production of telomers has the following distribution:

| | |
|---|---|
| $C_4F_9I$ | 0.3% |
| $C_6F_{13}I$ | 15.5% |
| $C_8F_{17}I$ | 45.8% |
| $C_{10}F_{21}I$ | 22.5% |
| $\geq C_{12}F_{25}I$ | 15.9% |

The productivity of $C_8F_{17}I$ reaches 72.4 g/h/l, but the selectivity falls to 1.2.

EXAMPLE C (Comparative)

The reactor of Example A is used, and is fed at the head with a mixture of 30.5 g/h of $C_2F_4$, 354.5 g/h of $C_2F_5I$, 184.4 g/h of $C_4F_9I$ and 193.8 g/h of $C_6F_{13}I$. At 350° C. an equilibrium is substantially obtained in terms of $C_4F_9I$ and $C_6F_{13}I$. The mass balances of input and output are collated in the following table:

| COMPONENT | INPUT (g/h/l) | OUTPUT (g/h/l) |
|---|---|---|
| $C_2F_4$ | 106 | 51.7 |
| $C_2F_5I$ | 1221.6 | 1179.6 |
| $C_4F_9I$ | 627.7 | 645.8 |
| $C_6F_{13}I$ | 667.8 | 673.9 |
| $C_8F_{17}I$ | 0.7 | 60.7 |
| $C_{10}F_{21}I$ | 0 | 8.4 |
| $\geq C_{12}F_{25}I$ | 0 | 1.2 |
| RfRf | 6 | 8.6 |

These operating conditions correspond to the reactor being fed with 54.3 g/h/l of fresh $C_2F_4$ and 42 g/h/l of fresh $C_2F_5I$. The production of telomers has the following distribution:

| | |
|---|---|
| $C_4F_9I$ | 19.3% |
| $C_6F_{13}I$ | 6.5% |
| $C_8F_{17}I$ | 64% |
| $C_{10}F_{21}I$ | 9.0% |
| $\geq C_{12}F_{25}I$ | 1.3% |

The productivity of $C_8F_{17}I$ reaches 60 g/h/l, and the selectivity is 6.25.

EXAMPLE 1

The same reactor is used as in Example A, but the telomers of extents 1 and 2 ($C_4F_9I$ and $C_6F_{13}I$) are introduced via an aperture situated at one-third the length of the tube.

At 350° C., substantially steady-state operation in terms of $C_4F_9I$ is achieved by feeding the reactor as follows:
- at the head of the reactor: 23.5 g/h of $C_2F_4$ and 130.1 g/h of $C_2F_5I$
- at ⅓ of the reactor: 231.4 g/h of $C_4F_9I$ and 265.16 g/h of $C_6F_{13}I$ The mass balances of input and output are collated in the following table:

| COMPONENT | INPUT (g/h/l) | OUTPUT (g/h/l) |
|---|---|---|
| $C_2F_4$ | 81.5 | 26.1 |
| $C_2F_5I$ | 448.8 | 399.2 |
| $C_4F_9I$ | 787.1 | 797.6 |
| $C_6F_{13}I$ | 911.8 | 925.5 |
| $C_8F_{17}I$ | 0.9 | 68.1 |
| $C_{10}F_{21}I$ | — | 7.4 |
| $\geq C_{12}F_{25}I$ | — | 1.7 |
| RfRf | 7.7 | 15.9 |

Under these conditions, which correspond to the reactor being fed with 55.4 g/h/l of fresh $C_2F_4$ and 49.6 g/h/l of fresh $C_2F_5I$, the production of telomers has the following distribution:

| | |
|---|---|
| $C_4F_9I$ | 10.4% |
| $C_6F_{13}I$ | 13.6% |
| $C_8F_{17}I$ | 66.9% |
| $C_{10}F_{21}I$ | 7.4% |
| $\geq C_{12}F_{25}I$ | 1.7% |

The selectivity is 7.35 for a productivity of $C_8F_{17}I$ of 67.2 g/h/l. In relation to Comparative Example A, the gains in selectivity and productivity are 5.6% and 26.8% respectively.

In relation to Example C, which was carried out with a substantially comparable flow rate of fresh reactants, the gains in selectivity and productivity are equal to 17.5% and 12% respectively.

EXAMPLE 2

Example 1 is repeated but with an aperture situated at one quarter the length of the tube.

At 350° C., steady-state operation is reached in terms of $C_4F_9I$ by feeding the reactor as follows:

at the head of the reactor: 23.7 g/h of $C_2F_4$ and 119.6 g/h of $C_2F_5I$ at ¼ of the reactor: 229.4 g/h of $C_4F_9I$ and 294.6 g/h of $C_6F_{13}I$ The mass balances of input and output are collated in the following table:

| COMPONENT | INPUT (g/h/l) | OUTPUT (g/h/l) |
|---|---|---|
| $C_2F_4$ | 81.7 | 28.2 |
| $C_2F_5I$ | 412.8 | 355.2 |
| $C_4F_9I$ | 780.3 | 780.0 |
| $C_6F_{13}I$ | 1013.1 | 1033.2 |
| $C_8F_{17}I$ | 1.0 | 78.7 |
| $C_{10}F_{21}I$ | — | 8.7 |
| $\geq C_{12}F_{25}I$ | — | 1.4 |
| RfRf | 8 | 13.3 |

Under these conditions, which correspond to the reactor being fed with 53.5 g/h/l of fresh $C_2F_4$ and 57.6 g/h/l of $C_2F_5I$, the production of telomers has the following distribution:

| | |
|---|---|
| $C_6F_{13}I$ | 18.6% |
| $C_8F_{17}I$ | 72% |
| $C_{10}F_{21}I$ | 8% |
| $\geq C_{12}F_{25}I$ | 1.3% |

The selectivity is 7.75 for a productivity of $C_8F_{17}I$ of 77.7 g/h/l.

In relation to Comparative Example A, the gains in selectivity and productivity are 11.4% and 46.6% respectively.

EXAMPLE 3

The same reactor is used as in Example B, with introduction of the telomers of extents 1 and 2 ($C_4F_9I$ and $C_4F_9I$) via an aperture situated at one-third the length of the tube.

At 340° C., substantially steady-state operation in terms of $C_4F_9I$ is attained by feeding the reactor as follows:

at the head of the reactor: 25.6 g/h of $C_2F_4$ and 94.4 g/h of $C_2F_5I$ at ⅓ of the reactor: 74.0 g/h of $C_4F_9I$ and 112.8 g/h of $C_6F_{13}I$ The mass balances of input and output are collated in the following table:

| COMPONENT | INPUT (g/h/l) | OUTPUT (g/h/l) |
|---|---|---|
| $C_2F_4$ | 102.4 | 28.5 |
| $C_2F_5I$ | 377.4 | 294 |
| $C_4F_9I$ | 292.1 | 320.3 |
| $C_6F_{13}I$ | 449.8 | 467.7 |
| $C_8F_{17}I$ | 0.4 | 81.9 |
| $C_{10}F_{21}I$ | 0 | 18.6 |
| $\geq C_{12}F_{25}I$ | 0 | 8.9 |
| RfRf | 2.8 | 4.3 |

Under these conditions, which correspond to the reactor being fed with 73.9 g/h/l of fresh $C_2F_4$ and 83.4 g/h/l of fresh $C_2F_5I$, the production of telomers has the following distribution:

| | |
|---|---|
| $C_4F_9I$ | 18.2% |
| $C_6F_{13}I$ | 11.6% |
| $C_8F_{17}I$ | 52.5% |
| $C_{10}F_{21}I$ | 12.0% |
| $\geq C_{12}F_{25}I$ | 5.7% |

The productivity of $C_8F_{17}I$ reaches 81.5 g/h/l and the selectivity is 2.96.

In relation to Example B, and for a substantially identical feed-flow rate of fresh reactants, graduated recycling increases the productivity of $C_8F_{17}I$ by 12.5%, whereas the selectivity is multiplied by 2.5.

We claim:

1. Continuous process for production of a particular perfluoroalkyl iodide RfI, Rf denoting a perfluoroalkyl radical which is linear and contains from 6 to 12 carbon atoms or is branched and contains from 7 to 13 carbon atoms, said perfluoroalkyl iodide being a telomer of formula $C_2F_5(CF_2CF_2)_nI$ or $(CF_3)_2CF(CF_2CF_2)_nI$ wherein n is an integer from 2 to 5, comprising:

thermally telomerizing in the gas phase, in a tubular reactor, tetrafluoroethylene with a telogen reactant of formula $C_2F_5(CF_2CF_2)_{n'}I$ or $(CF_3)_2CF(CF_2CF_2)_{n'}I$ wherein n' is an integer from 0 to 3, but is less than n-1, and recycling intermediate telomers of formula $C_2F_5(CF_2CF_2)_{n''}I$ or $(CF_3)_2CF(CF_2CF_2)_{n''}I$ wherein n'<n''<n which were formed during said thermal telomerization to at least one point of the reactor which is situated between one-twentieth and three-quarters the length of the reactor, the distances being taken from the reactor inlet.

2. Process according to claim 1, wherein the intermediate telomers are recycled to at least one point of the tube which is situated between one-fifth and two-fifths of its length.

3. Process according to claim 1, wherein the intermediate telomers are recycled to different points of the reactor, lighter telomers in an upstream zone of reactor and the heavier ones in a downstream zone.

4. Process according to claim 3, wherein the upstream zone is situated between one-twentieth and one-third of the length of the reactor and the downstream zone is situated between one-fifth and half the length of the reactor.

5. Process according to claim 1, wherein the ratio of length to internal diameter of the reactor is between 50 and 5,000.

6. Process according to claim 1, wherein telomerization is carried out at a temperature ranging from 300° to 360° C.

7. Process according to claim 1, wherein the molar ratio of fresh telogen to fresh $C_2F_4$ is between 0.1 and 0.6.

8. Process according to claim 1, wherein one portion of the tetrafluoroethylene is injected at at least one point of the reactor which is situated between two-fifths and three-quarters the length of the reactor, the remainder being introduced at the head of the reactor at the same time as a starting telogen.

9. Process according to claim 1, wherein the feeding of the reactor with fresh and/or recycled reactants is regulated such that, in steady-state operation, the quantities of intermediate telomer with n"=n'+1 entering and leaving the reactor are substantially identical.

10. Process according to claim 1, wherein perfluorooctyl iodide $C_8F_{17}I$ is produced.

11. Process according to claim 6, wherein the temperature range is between about 325° and 355° C.

12. Process according to claim 7, wherein the molar ratio is between 0.2 and 0.5.

13. Process according to claim 1 wherein the tubular reactor has a ratio of length to internal diameter of between 50 and 5,000, and at least one aperture for recycling intermediate telomers, said reactor being heated homogeneously to a temperature of between 300° C. and 360° C.

14. Process according to claim 13 wherein all of the intermediate telomers are recycled to the same point in the tubular reactor.

15. Process according to claim 13 further comprising the steps of:

introducing products exiting the reactor into a soak column to separate unconverted tetrafluoroethylene and telogen reactants, recycling the separated unconverted tetrafluoroethylene and telogen reactants to the head of the reactor, fractionating in first column to separate the intermediate telomers, recycling the separated intermediate telomers to the reactor, and fractionating the remaining telomers in a second column to separate the particular RfI from the heavier products.

16. Continuous process for production of a particular perfluoroalkyl iodide RfI, Rf denoting a perfluoroalkyl radical which is linear and contains from 6 to 12 carbon atoms or is branched and contains from 7 to 13 carbon atoms, said perfluoroalkyl iodide being a telomer of formula $C_2F_5(CF_2CF_2)_nI$ or $(CF_3)_2CF(CF_2CF_2)_nI$ wherein n is an integer from 2 to 5 comprising the steps of:

in the gas phase in a tubular reactor having a plurality of apertures, thermally telomerizing tetrafluoroethylene with a telogen reactant of formula $C_2F_5(CF_2CF_2)_{n'}I$ or $(CF_3)_2CF(CF_2CF_2)_{n'}I$ wherein n' is an integer from 0 to 3, but is less than n-1, at a molar ratio of fresh telogen reactant to fresh tetrafluoroethylene of between 0.1 and 0.6, one portion of the tetrafluoroethylene being injected at at least one point of the reactor which is situated between two-fifths and three-quarters the length of the reactor, the remainder being introduced at the head of the reactor at the same time as the starting telogen, and recycling intermediate telomers of formula $C_2F_5(CF_2CF_2)_{n"}I$ or $(CF_3)_2CF(CF_2CF_2)_{n"}I$ wherein n'<n"<n which were formed during said thermal telomerization to different ones of the apertures, lightest telomers being injected between one-twentieth and one-third the length of the tubular reactor, and heaviest telomers being injected between one-fifth and one-half the length of the tubular reactor, the distances being taken from the reactor inlet.

17. Process according to claim 16 wherein the molar ratio of fresh telogen reactant to fresh tetrafluoroethylene is between 0.2 and 0.5.

18. Process according to claim 16, wherein the feeding of the reactor with fresh and/or recycled reactants is regulated such that, in steady-state operation, the quantities of intermediate telomers entering and leaving the reactor are substantially identical.

19. Process according to claim 16 further comprising the steps of:

introducing products exiting the reactor into a soak column to separate unconverted tetrafluoroethylene and telogen reactants, recycling the separated unconverted tetrafluoroethylene and telogen reactants to the head of the reactor, fractionating in first column to separate the intermediate telomers, recycling the separated intermediate telomers to the reactor, and fractionating the remaining telomers in a second column to separate the particular RfI from heavier products.

20. Continuous process for production of perfluorooctyl iodide $C_8F_{17}I$, comprising:

thermally telomerizing in the gas phase, in a tubular reactor, tetrafluoroethylene with pentafluoroethyl iodide $C_2F_5I$, and recycling intermediate telomers, including $C_4F_9I$ and $C_6F_{13}I$, which were formed during said thermal telomerization to at least one point of the reactor which is situated between one-twentieth and three-quarters the length of the reactor, the distances being taken from the reactor inlet.

21. Process according to claim 20, wherein the intermediate telomers are recycled to at least one point of the reactor which is situated between one-fifth and two-fifths of its length.

22. Process according to claim 20, wherein the intermediate telomers are recycled to different points of the reactor, lighter telomer in an upstream zone of the reactor and heavier one in a downstream zone.

23. Process according to claim 22, wherein the upstream zone is situated between one-twentieth and one-third of the length of the reactor and the downstream zone is situated between one-twentieth and one-third of the length of the reactor.

24. Process according to claim 20, wherein the ratio of length to internal diameter of the reactor is between 50 and 5,000.

25. Process according to claim 20, wherein telomerization is carried out at a temperature ranging from 300° to 360° C.

26. Process according to claim 20, wherein the molar ratio of pentafluoroethyl iodide $C_2F_5I$ to tetrafluoroethylene $C_2F_4$ is between 0.1 and 0.6.

27. Process according to claim 20, wherein one portion of the tetrafluoroethylene is injected at at least one point of the reactor which is situated between two-fifths and three-quarters in length of the reactor, the remainder being introduced at the head of the reactor at the same time as the pentafluoroethyl iodide.

28. Process according to claim 20, wherein the feeding of the reactor with fresh and/or recycled reactants is regulated such that, in steady-state operation, the quantities of perfluorobutyl iodide $C_4F_9I$ entering and leaving in the reactor are substantially identical.

29. Process according to claim 25, wherein the temperature range is between about 325° and 355° C.

30. Process according to claim 26, wherein the molar ratio is between 0.2 and 0.5.

31. Process according to claim 20, wherein the tubular reactor has a ratio of length to internal diameter of between 50 and 5,000 and at least one aperture for recycling intermediate telomers, said reactor being heated homogeneously to a temperature of between 300° C. and 365° C.

32. Process according to claim 31, wherein all of the intermediate telomers are recycled to the same point in the tubular reactor.

33. Process according to claim 31 further comprising the steps of:

introducing products exiting the reactor into a soak column to separate unconverted tetrafluoroethylene and pentafluoroethyl iodide, recycling the separated unconverted tetrafluoroethylene and pentafluoroethyl iodide to the head of the reactor, fractionating in first column to separate the intermediate telomers, recycling intermediate telomers to the reactor, and fractionating the remaining telomers in a second column to separate the perfluorooctyl iodide from the heavier products.

34. Continuous process for production of perfluorooctyl iodide $C_8F_{17}I$, comprising the steps of:

in the gas phase in a tubular reactor having a plurality of apertures, thermally telomerizing tetrafluoroethylene with pentafluoroethyl iodide $C_2F_5I$, at a molar ratio of fresh pentafluoroethyl iodide to fresh tetrafluoroethylene of between 0.1 and 0.6, one portion of the tetrafluoroethylene being injected at at least one point of the reactor which is situated between two-fifths and three-quarters the length of the reactor, the remainder being introduced at the head of the reactor at the same time as the pentafluoroethyl iodide, and recycling intermediate telomers, including $C_4F_9I$ and $C_6F_{13}I$, which were formed during said thermal telomerization to different ones of the apertures, the lightest telomer being injected between one-twentieth and one-third the length of the tubular reactor, and the heaviest telomer being injected between one-fifth and one-half the length of the tubular reactor, the distances being taken from the reactor inlet.

35. Process according to claim 34, wherein the feeding of the reactor with fresh and/or recycled reactants is regulated such that, in steady-state operation, the quantities of perfluorobutyl iodide entering and leaving the reactor are substantially identical.

36. Process according to claim 34, further comprising the steps of:

introducing products exiting the reactor into a soak column to separate unconverted tetrafluoroethylene and pentafluoroethyl iodide, recycling the separated unconverted tetrafluoroethylene and pentafluoroethyl iodide to the head of the reactor, fractionating in first column to separate intermediate telomers, recycling the separated intermediate telomers to the reactor, and fractionating the remaining telomers in a second column to separate the perfluorooctyl iodide from heavier products.

37. Process according to claim 34, wherein the molar ratio of fresh pentafluoroethyl iodide to fresh tetrafluoroethylene is between 0.2 and 0.5.

38. Continuous process for production of a perfluoroalkyl iodide RfI, Rf denoting a perfluoroalkyl radical which is linear and contains from 6 to 12 carbon atoms or is branched and contains from 7 to 13 carbon atoms, said RfI being a particular high telomer from tetrafluoroethylene with a telogen reactant selected from the group consisting of pentafluoroethyl iodide, heptafluoroisopropyl iodide and low telomers thereof, comprising:

thermally telomerizing tetrafluoroethylene with said telogen reactant in the gas phase, in a tubular reactor, and recycling intermediate telomers which were formed during said thermal telomerization to at least one point of the reactor which is situated between one-twentieth and three-quarters the length of the reactor, the distances being taken from the reactor inlet.

39. Continuous process for production of a perfluoroalkyl iodide RfI, Rf denoting a perfluoroalkyl radical which is linear and contains from 6 to 12 carbon atoms or is branched and contains from 7 to 13 carbon atoms, said RfI being a particular high telomer from tetrafluoroethylene with a telogen reactant selected from the group consisting of pentafluoroethyl iodide, heptafluoroisopropyl iodide and low telomers thereof, comprising the steps of:

in gas phase in a tubular reactor having a plurality of apertures, thermally telomerizing tetrafluoroethylene with said telogen reactant, at a molar ratio of fresh telogen reactant to fresh tetrafluoroethylene of between 0.1 and 0.6, one portion of the tetrafluoroethylene being injected at at least one point of the reactor which is situated between two-fifths and three-quarters the length of the reactor, the remainder being introduced at the head of the reactor at the same time as the starting telogen, and recycling intermediate telomers which were formed during said thermal telomerization to different ones of the apertures, lightest telomers being injected between one-twentieth and one-third the length of the tubular reactor, and heaviest telomers being injected between one-fifth and one-half the length of the tubular reactor, the distances being taken from the reactor inlet.

\* \* \* \* \*